(12) United States Patent
Hancock et al.

(10) Patent No.: US 8,187,191 B2
(45) Date of Patent: May 29, 2012

(54) SYSTEM AND METHOD FOR EQUALIZING RECEIVED INTRAVASCULAR ULTRASOUND ECHO SIGNALS

(75) Inventors: Andrew Hancock, Sacramento, CA (US); Dale Gene Dorando, Shingle Springs, CA (US)

(73) Assignee: Volcano Corporation, Rancho Cordova, CA (US)

( * ) Notice: Subject to any disclaimer, the term of this patent is extended or adjusted under 35 U.S.C. 154(b) by 697 days.

(21) Appl. No.: 12/350,774

(22) Filed: Jan. 8, 2009

(65) Prior Publication Data

US 2010/0174190 A1 Jul. 8, 2010

(51) Int. Cl.
*A61B 8/00* (2006.01)

(52) U.S. Cl. ........ 600/443; 600/407; 600/437; 600/446; 600/463; 382/128

(58) Field of Classification Search .......... 600/443–445, 600/437, 407, 466–467; 382/128
See application file for complete search history.

(56) References Cited

U.S. PATENT DOCUMENTS

| 4,075,883 | A | * | 2/1978 | Glover | 73/607 |
| 4,917,097 | A | * | 4/1990 | Proudian et al. | 600/463 |
| 5,549,111 | A | * | 8/1996 | Wright et al. | 600/443 |
| 2008/0294046 | A1 | * | 11/2008 | Chiang et al. | 600/447 |

* cited by examiner

*Primary Examiner* — Tse Chen
*Assistant Examiner* — Joel F Brutus
(74) *Attorney, Agent, or Firm* — Haynes and Boone, LLP

(57) ABSTRACT

A system and method are disclosed for providing an equalized ultrasound echo signal for the rendering intravascular images. The system includes an ultrasound catheter including an ultrasound transducer probe. An intravascular ultrasound console receives an ultrasound echo signal corresponding to reflections of an ultrasound signal by backscatterers. An ultrasound echo signal time-gain compensation equalizer compensates the ultrasound echo signal according to sub-bands within a frequency response spectrum of the ultrasound echo signal. After applying selective amplifier gains on the sub-bands, the sub-band signals are combined to create an equalized ultrasound echo signal.

33 Claims, 7 Drawing Sheets

SYSTEM AND METHOD FOR EQUALIZING RECEIVED INTRAVASCULAR ULTRASOUND ECHO SIGNALS

FIELD OF THE INVENTION

The present invention generally relates to the field of imaging systems, and more particularly to intravascular ultrasound imaging systems and methods for processing intravascular ultrasound echo signals in order to render image data facilitating diagnosis of vascular disease.

BACKGROUND

The development of new medical technologies has provided an increasing number of options available to doctors for the diagnosis and treatment of cardiovascular diseases. The availability of such equipment has improved the ability of doctors and surgeons to detect/diagnose and treat cardiovascular disease. Intravascular imaging technologies have enabled doctors to create and view a variety of images generated by a sensor inserted within a vasculature. Such images complement traditional radiological imaging techniques such as angiography by providing images of the tissue and/or blood flow within vessels rather than showing a two dimensional lumen image such as the type rendered by an angiogram.

Intravascular ultrasound (IVUS) analysis finds particular application to a system and method for quantitative component identification within a vascular object including characterization of tissue as well as identification of fluid flow in a particular cross-section of a lumen. It should be appreciated that while the exemplary embodiment is described in terms of an ultrasonic device, or more particularly the use of IVUS data (or a transformation thereof) to render images of a vascular object, the present disclosure is not so limited. Thus, for example, using backscattered data (or a transformation thereof) based on ultrasound waves or even electromagnetic radiation (e.g., light waves in non-visible ranges such as Optical Coherence Tomography, X-Ray CT, etc.) to render images of any tissue type or composition (not limited to vasculature, but including other human as well as non-human structures) is within the spirit and scope of the present disclosure.

Imaging portions of a patient's body provides a useful tool in various areas of medical practice for determining the best type and course of treatment. Imaging of the coronary vessels of a patient by techniques involving insertion of a catheter-mounted probe (e.g., an ultrasound transducer array) can provide physicians with valuable information. For example, the image data indicates the extent of a stenosis in a patient, reveals progression of disease, and helps determine whether procedures such as angioplasty or atherectomy are indicated or whether more invasive procedures are warranted.

In an intravascular ultrasound imaging system, an ultrasonic transducer probe is attached to a distal end of a catheter that is carefully maneuvered through a patient's body to a point of interest such as within a coronary artery. The transducer probe in known systems comprises piezoelectric crystal, PVDF or a Capacitive Micro Ultrasound Transducer (CMUT). The transducer probe in known systems is either a single element that is mechanically scanned or rotated back and forth to cover a sector over a selected angular range. Acoustic signals are transmitted and echoes (or backscatter) from these acoustic signals are received. The backscatter data is used to identify the type or density of a scanned tissue. As the probe is swept through the sector, many acoustic lines (emanating from the probe) are processed to build up a sector-shaped cross-section image of tissue within the patient. After the data is collected, an image of the blood vessel (i.e., an IVUS image) is reconstructed using well-known techniques. This image is then visually analyzed by a cardiologist to assess the vessel components, blood-flow cross-sectional area, and plaque content. Other known systems acquire ultrasound echo data using a probe comprising an array of transducer elements that are mechanically and/or electronically scanned to cover a sector over a selected angular range.

In a particular application of IVUS imaging, ultrasound data is used to characterize tissue within a vasculature and produce images graphically depicting the content of the tissue making up imaged portions of a vessel. Examples of such imaging techniques for performing spectral analysis on ultrasound echoes to render a color-coded tissue map are presented in Nair et al. U.S. Pat. No. 7,074,188 entitled "System and Method of Characterizing Vascular Tissue" and Vince et al. U.S. Pat. No. 6,200,268 entitled "Vascular Plaque Characterization", the contents of which are incorporated herein by reference in their entirety, including any references contained therein. Such systems analyze response characteristics of ultrasound backscatter (reflected sound wave) data to identify a variety of tissue types found in partially occluded vessels including: fibrous tissue, fibro-fatty, necrotic core, and dense calcium. An example of a known plaque characterization imaging technique is referred to as "virtual histology" (VH).

When characterizing the response of tissue that has been subjected to ultrasound waves, parameter values are considered at a data point in an imaged field. Based upon response characteristics (e.g., power spectra) of known tissue types, tissue at the data point is assigned to a particular tissue type (e.g. necrotic core). Known systems utilize an integrated backscatter parameter that represents a power response over a frequency band. The integrated backscatter parameter generally represents a measure of total reflected ultrasound power at a particular point within a vasculature over a specified frequency band.

As a transmitted ultrasound signal travels through space within a body, several factors (e.g., spreading (beam diffraction), scattering, absorption, etc.) cause attenuation of the originally transmitted signal. Previously, a time-gain compensation (TGC) signal processing stage (step) in an IVUS echo signal processing chain amplified all frequencies at a given time of receipt (corresponding to a particular range/distance from the transducer element) equally.

SUMMARY OF THE INVENTION

Attenuation of an IVUS signal varies with frequency. Therefore, lower frequency components of an IVUS signal are comparatively less susceptible to attenuation than higher frequency components and applying a single amplification to all frequency components of a received signal enhances those differences. To prevent loss of signal fidelity, saturation, and other artifacts associated with amplifying IVUS signals equally at all frequency components, in accordance with the present invention, a method and computer system operating according to computer-executable instructions read from a physical computer-readable medium are disclosed for applying a multi-band equalizer/amplifier to received IVUS echo signal streams to compensate the signal attenuation at particular frequency bands and time ranges.

More particularly, IVUS echo signal attenuation is compensated by initially processing a received IVUS echo signal (e.g., a time-order digitized echo signal data stream) to render N sets of echo signal data streams corresponding to N frequency sub-bands. Thereafter, a set of N gain constants are applied to the N sets of echo signal data corresponding to the N frequency bands. In an illustrative embodiment, the N gain constants are also range (time) dependent. The result is a set of N equalized sets of echo signal data for a given time-gain compensation range.

Thereafter, a summing operation/step combines the N equalized sets of echo signal data into a single time-gain compensated and frequency band-equalized IVUS echo signal segment (corresponding to a particular time-gain range).

The invention is implemented in a computer system that is configured with a computer-readable medium including computer-executable instructions to carry out the aforementioned steps.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

Figure 6:
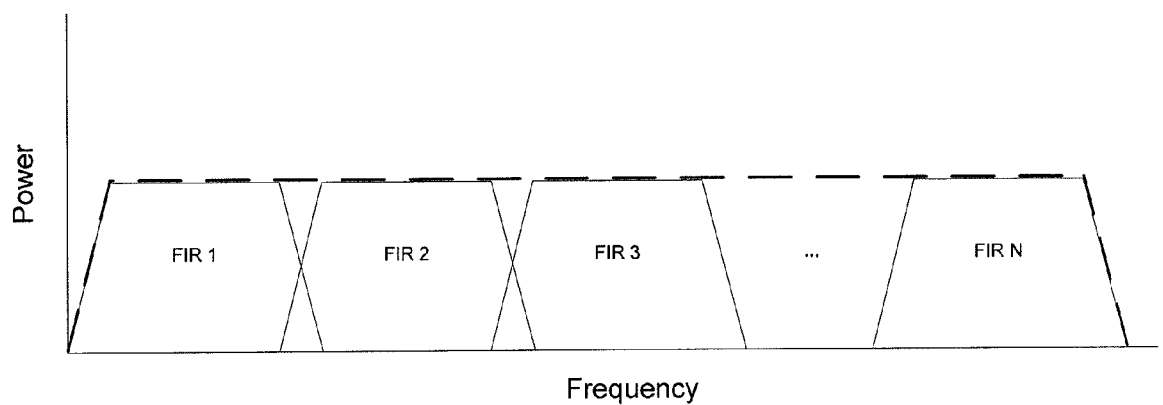
FIG. 6 illustratively depicts an exemplary frequency response of a set of N filters contained within the sub-system depicted in FIG. 5.

Before turning to the drawings a brief discussion of the basic principles of operation of an IVUS echo signal processing method and equalizer device are briefly described. The time-gain compensation equalizer disclosed herein operates upon N sets of echo signal segment data corresponding to N distinct frequency range components of a transduced IVUS echo signal. Equalizing the N sets of echo signal segment data increases signal dynamic range/signal fidelity by separating the signal into partially overlapping (see, FIG. 6 described herein below) frequency range-specific bins, performing frequency-bin dependent signal amplification (equalization) over a TGC range, and then recombining the frequency bins into a single signal. Equalization of frequency-dependent components of a received IVUS echo segment is therefore applied to compensate for attenuation occurring at each frequency band.

Regarding the signal processor component (implemented in hardware/software/firmware) used to carry out the above-described equalization, in an exemplary embodiment described herein, an N-band ultrasound equalizer utilizes N (e.g., 5) filters to process a transduced IVUS echo signal into N frequency bins. The number amplifiers (N) may be odd or even. However, using an odd number of amplifiers enables the middle filter to operate upon a component of the transduced IVUS echo signal that corresponds to the transducers' center frequency. The disclosed equalizer processing component is potentially implemented with analog circuitry, but is preferably carried out via digital data processing hardware/firmware/software that operates upon streams of digitized signal data corresponding to transduced IVUS echo signals based upon a set of range-dependent frequency bin-specific amplification coefficients.

By way of example, N amplifiers are applied to echo signal data contained in corresponding ones of the N frequency bins to boost/attenuate the signal in each frequency bin independently. In an exemplary embodiment, each of the N amplifiers is range adjusted so that a separate gain is specified for each range. In the exemplary embodiment, the coefficients that drive amplification in each of the N amplifiers are pre-programmed (i.e., not user adjustable). The relatively static nature of the equalizer coefficient contrasts with an amplifier coefficient associated with an overall TGC control which is applied to the entire IVUS echo signal.

The equalized signals from the N frequency bins are summed to render an equalized IVUS echo signal. In an illustrative embodiment, a second TGC amplification stage amplifies the equalized IVUS echo signal in accordance with a second TGC coefficient. The second TGC coefficient is user adjustable. The second TGC coefficient corresponds to the user TGC controls of the current range-based amplification adjustments incorporated into existing IVUS imaging systems. It is further noted that it is not necessary to have two separate amplifier stages. In other embodiments the equalization amplifier stage amplifies each frequency band-specific component of the IVUS echo signal based upon a summed amplification coefficient that represents the combination of the band-specific equalization coefficient and user-adjustable generalized TGC coefficient. Furthermore, the generalized TGC amplification stage can alternatively be applied to the received IVUS echo signal prior to a stage where the echo signal is separated into the N distinct bands.

The above-described equalization procedure/processor component provides an improved image that suffers less from saturation. The equalization also improves the ability to visualize lower amplitude signals near a noise floor. It is also noted that while the above-described signal processing is carried out on-line in real time to render an image from the equalized signal data, in other embodiments the equalizer is applied off-line on transduced IVUS echo signal data as a pre-processing step for generating an off-line image (e.g., generation of a colorized cross-sectional image based on a virtual histology analysis of the IVUS echo signal data).

In the detailed description of the exemplary embodiment that follows, like element numerals are used to describe like elements illustrated in one or more figures.

Figure 1:
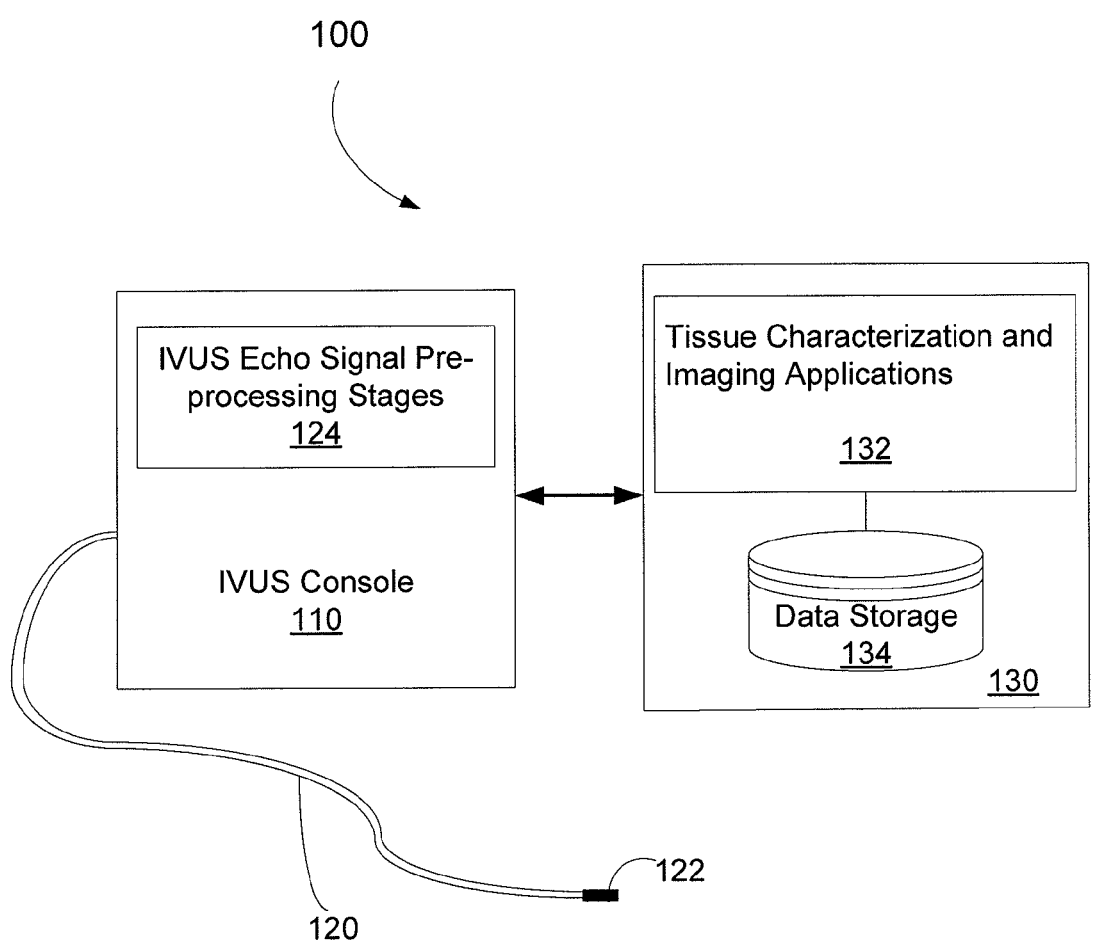
FIG. 1 illustratively depicts a IVUS system including a programmed computer that generates, from received transduced echo signal segments, equalized time-gain compensated IVUS echo signal data.

Turning to FIG. 1, an IVUS echo signal data acquisition and processing system 100 is schematically depicted. An intravascular ultrasound console 110 is communicatively coupled to an IVUS catheter 120. The IVUS catheter 120 comprises a distally mounted ultrasound transducer probe 122 that acquires backscatter data (e.g., IVUS data) from a blood vessel. In accordance with known IVUS catheters, the catheter 120 is maneuvered through a patient's body (e.g., via a femoral artery) to a point of interest. The transducer probe 122 is then controlled, via the console 110 to emit ultrasound pulses and thereafter receive echoes or backscattered signals reflected from vascular tissue/plaque and blood. Because different types and densities of tissue absorb and reflect (backscatter) the ultrasound pulse differently, the reflected ultrasound echo data (i.e., IVUS data) signals transmitted back to the console 110 by the IVUS catheter 120, are converted by characterization software into images of vascular objects. It should be appreciated that the IVUS console 110 depicted herein is not limited to any particular type of IVUS console, and includes all ultrasonic devices known to those skilled in the art (e.g., In-Vision Gold and s5™ systems of Volcano Corporation). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

The system depicted in FIG. 1 includes IVUS echo signal conditioning stages 124 including computer-executable instructions/operations embodied in hardware/firmware/software that pre-process received analog IVUS echo signal segments for use by tissue characterization and imaging applications 132. Preprocessing includes a variety of filtering and amplification operations described further herein below. The aforementioned multi-band equalization operation is one of a sequence of operations carried out by the conditioning stages 124.

It is noted that the equalization operation can be applied to either a single echo signal segment (see, e.g., FIG. 2) or to a summed set of received IVUS echo signals (e.g., flow imaging mode) combined with temporal/spatial neighbors to render values that exhibit improved signal/noise ratios. Thus, multiple echo signal segments from adjacent scan lines or repeated firings on a same scan line can be combined and processed by the equalization processing stage described herein.

Known imaging applications, maintained in the form of computer-executable instructions on a computer readable medium (e.g., hardware, firmware, software, etc.) executed on an IVUS console (e.g., console 110) or a communicatively coupled computing device (e.g., computing device 130), render a variety of image types from received IVUS echo signal information rendered by the IVUS echo signal conditioning stages 124. A first type of imaging application converts ultrasound echo signal data into gray scale images reflecting the relative strength of the echo signal returned by the objects within the transducer probe 122's field of view. In such imaging applications, the relatively light and dark regions indicate different tissue types and/or densities. A second type of imaging application generates a cross-sectional image of a blood vessel lumen that indicates regions of blood flow. The first and second type of imaging applications are generally executed by one or more programmed processors on the console 110 to render the aforementioned gray scale and blood flow images.

Other imaging applications, such as tissue characterization and imaging applications 132, include computer executable instructions executed on the computing device 130 communicatively coupled to console 110. The applications 132 include a tissue characterization application that renders tissue type information based upon the spectral (e.g., frequency and power) characteristics of the IVUS echo information received by the console 110 from the catheter 120. The tissue characterization and imaging applications 132 generally operate online, but at a non-real time rate (e.g., with a few seconds delay), to render images based upon IVUS echo signal data rendered by the IVUS echo signal conditioning stages 124.

Figure 2:
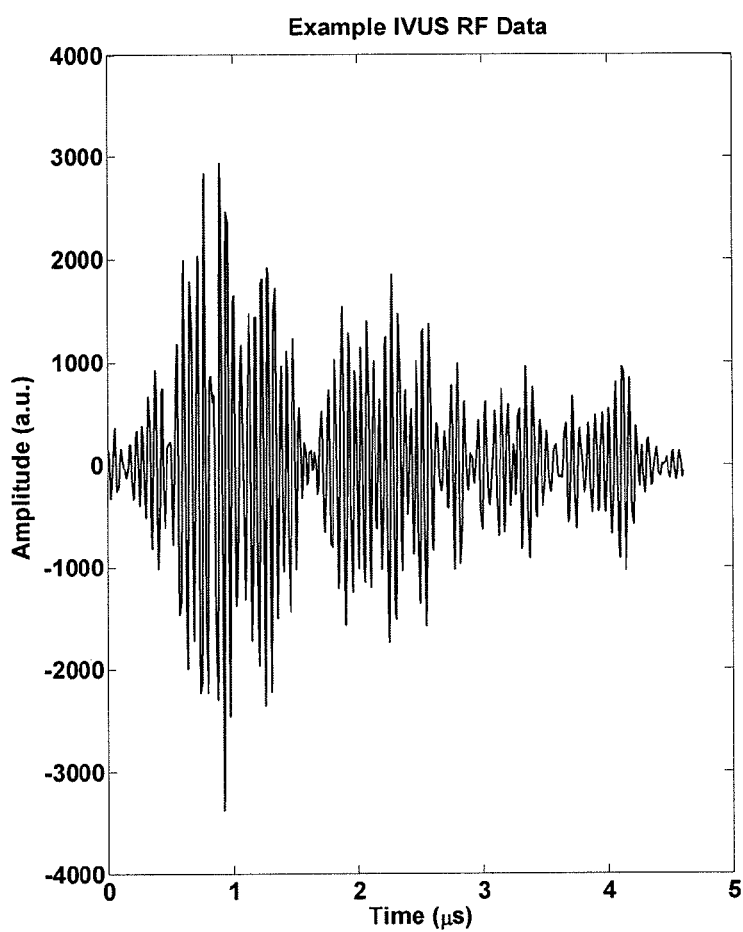
FIG. 2 graphically depicts an exemplary transduced IVUS echo signal's amplitude over a period of time.

With reference to FIG. 2, in an exemplary embodiment a portion of a transduced received IVUS echo signal is digitized and provided to further signal preprocessing stages. Such signal preprocessing stages, described herein below, include the aforementioned TGC stage including the multi-band equalizer/amplifier components.

Figure 3:
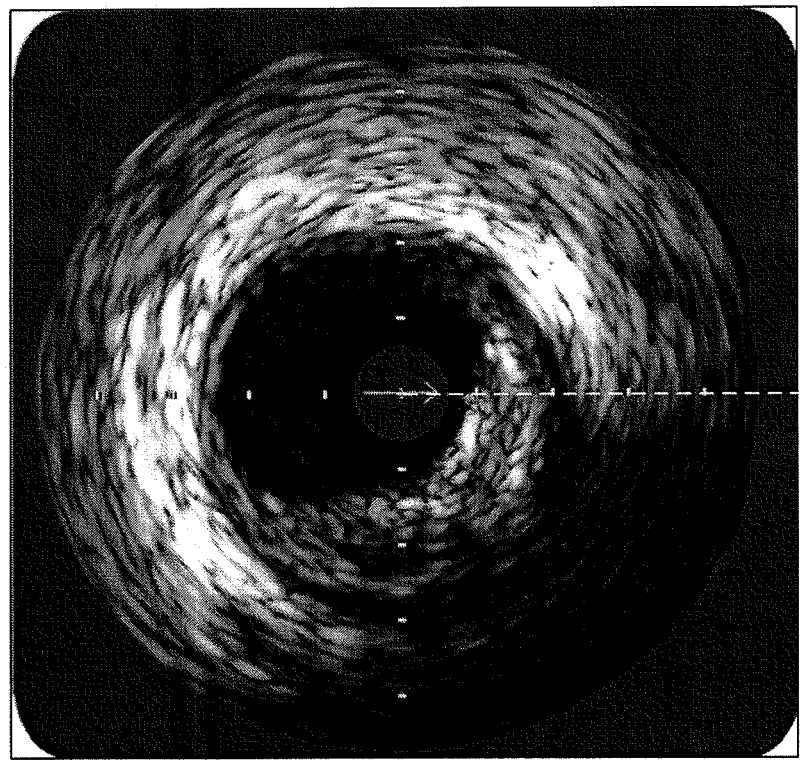
FIG. 3 is an exemplary grayscale ultrasound image of a vessel's cross-section.

Turning briefly to FIG. 3 showing an exemplary gray-scale IVUS image, in an exemplary embodiment, the system 100 correlates a time of receipt of the bracketed echo signal segment with a range (distance from a transducer element) along a scan line (the dotted horizontal line) in a field of view of an ultrasound probe. The aforementioned time/range is referenced herein in the context of the time-gain compensation (TGC) and equalization procedures/processes. The TGC stage accounts for attenuation of echo signals that occurs as the IVUS echo signals are received from progressively greater distances. Without the TGC stage, the brightness mode image would be progressively dimmer at greater distances from the transducer elements of the IVUS probe.

A data storage 134 stores the processed IVUS echo signal data rendered by the IVUS echo signal conditioning stages 124 and resulting image data rendered by the applications 132. The data storage 134 is, by way of example, any of a variety of data storage devices, including RAM, cache memory, flash memory, magnetic disks, optical disks, removable disks, SCSI disks, IDE hard drives, tape drives, optically encoded information discs (e.g., DVD) and all other types of data storage devices (and combinations thereof, such as RAID devices) generally known to those skilled in the art.

In the illustrative example, the tissue characterization and imaging applications 132 exist as a set of one or more applications executed on one or more computing devices (including multiple processor systems as well as groups of networked computers). The location of the applications 132 is not critical. Moreover, the number and location of the components depicted in FIG. 1 are not intended to limit the present invention, and are merely provided to illustrate, by way of example, the environment in which an exemplary system operates. Thus, for example, a computing device having a plurality of data storage devices and/or a remotely located characterization application (either in part or in whole) is within the spirit and scope of the present invention.

Figure 4:
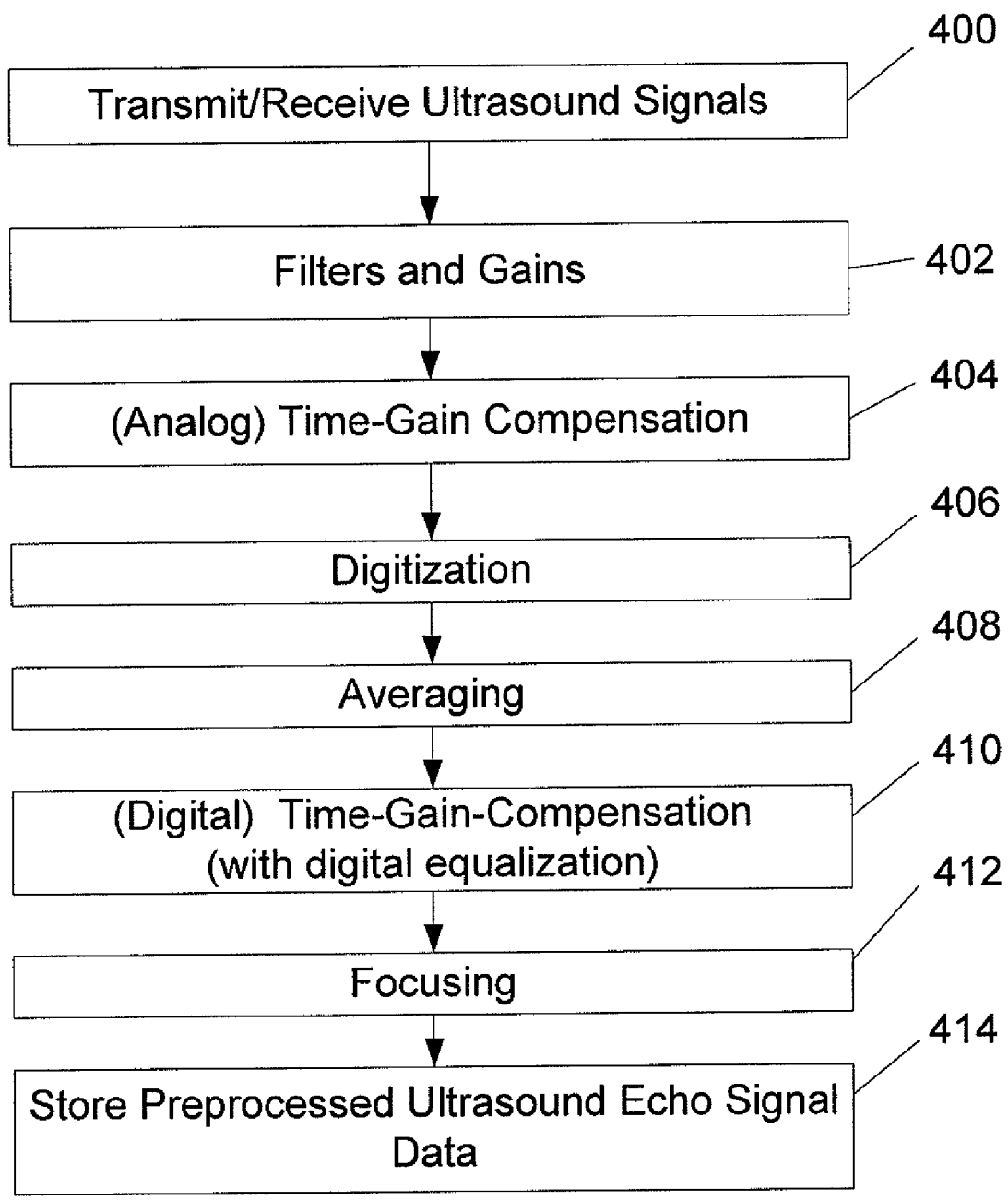
FIG. 4 is a flowchart summarizing an exemplary set of steps for generating a set of preprocessed ultrasound echo signal data forming the basis of later generated ultrasound images.

FIG. 4 summarizes an exemplary set of preprocessing stages for rendering time-gain compensated IVUS echo data from raw IVUS echo signals received by the IVUS console 110 from the IVUS catheter 120 during an imaging procedure. The summarized steps render properly conditioned data to support image construction in a variety of imaging modes including: gray scale, flow, and tissue characterization. The steps are initially described without specific reference to the aforementioned equalization procedure. Thereafter, two exemplary alternative ways for rendering equalized ultrasound echo signal data are described in relation to the described steps of FIG. 4.

During step 400 the ultrasound probe 122 transmits ultrasound pulses and receives ultrasound echo signals from scatterers within the field of view defined by a set of scan lines.

The received analog echo signals are passed via lead lines within the catheter 120 from the probe 122 to a patient interface module (PIM) wherein, during step 402, the signals are initially filtered and amplified. The purpose of this stage is to remove frequency components that constitute known noise (at both high and low frequency ranges).

Also within the PIM, during step 404, the analog signals are time-gain compensated a first time via analog amplifier circuitry within the PIM to accommodate the inherent drop off of reflected energy as a function of distance traveled by emitted ultrasound in its path of travel from/to the ultrasound probe. Generally time-gain compensation amplification occurs after removal of noise components. However, steps 402 and 404 are interchangeable in other embodiments. Also, with other embodiments, both steps 402 and 404 are performed at the console 110 rather than within the PIM.

Thereafter, during step 406 the filtered/amplified analog data signal is digitized. In an exemplary embodiment a 16 bit signed digital value is stored for each sample (taken at a sampling rate of 100 Msamples/sec). However, the sampling rate and precision of the digitized samples differs in alternative embodiments. For example, a precision of 12 bits is deemed acceptable (though not favored over 16 bit). Furthermore, in accordance with various embodiments, a sampling period for generating individual digital data points from the ultrasound echo signal corresponding to a scan line of back-scattered ultrasound data is in a range corresponding to the operating frequency and bandwidth of the ultrasound transducer. By way of example, for a 20 MHz transducer, the range is 2.5 to 10 nanoseconds (100 to 400 Msamples/sec). For a 10 MHz transducer the range is 5 to 20 nanoseconds (50 to 200 Msamples/sec). For a 40 MHz transducer, the range is 1.25 to 5 nanoseconds (200 to 800 Msamples/sec). In these examples, it is assumed sampling is 4 to 16 times the maximum frequency within the bandwidth of the transducer, which is assumed to be 50% of the center frequency. However, other sampling periods are contemplated in alternative embodiments.

In an exemplary embodiment, an averaging operation is performed on the digitized data during step 408 to improve a signal to noise ratio of the digitized data. The averaging, by way of example, comprises repeating the steps 400, 402, 404, 406 multiple times and thereafter summing together the resulting sets of digitized conditioned IVUS echo signals.

During step 410 additional time-gain compensation is applied to the digitized data signal. During this second TGC stage, a digital equalization procedure is potentially applied according to a set of coefficients that are specified by time and frequency range/bin.

Next, during step 412 a focusing operation is performed to render additional echo image data. Focusing (i.e., beamforming) combines signals from a neighborhood of array elements in order to improve sensitivity. A similar process can be performed with consecutive transmissions when using an ultrasonic probe that is comprised of a single element. Thus, while a signal segment is referred to herein in singular form, the ultrasound echo signal segment referred to herein is potentially a sum of multiple spatial or temporal ultrasound echo signals received by the IVUS system.

The above-described illustrative order of performing steps 410 and 412 is not essential, thus in alternative embodiments, TGC amplification step 410 is performed after the focusing step 412.

During step 414 the preprocessed digitized IVUS echo signal data is stored in a pre-processed echo signal buffer. The pre-processed echo signal buffer data is potentially used by any of a variety of imaging operations/applications including, for example, gray-scale and virtual histology image generation.

Equalizing the IVUS echo signals using analog equalization circuitry can be applied in any one of many stages of the IVUS echo signal processing path. By way of example, using the set of steps depicted in FIG. 4 as a guide, in embodiments utilizing analog equalizer components, the equalization step can be carried out before the digitization step 406. Furthermore, equalization can occur before or after virtually any of the steps illustratively depicted in FIG. 4 including: bandpass, high pass or low pass filtering steps used to remove signal components outside the operating band of the ultrasound transducer probe/element(s) (e.g., step 404); signal attenuation/amplification steps that are carried out on all signal components (e.g., by modifying currently used standard TGC stages that would correspond to steps 402, 404 and 412—without equalization); and signal log compression steps that are potentially performed during post-processing stages but in some embodiments are performed during IVUS echo signal pre-processing prior to digitization step 406.

Furthermore, in embodiments using an analog equalizer, N filters are used. The N filters are of Mth order, and of the same filter type (i.e. Chebyshev Type I, II, Butterworth, Bessel, etc.). In a particular exemplary embodiment of analog equalization, $5^{th}$ order Bessel filters are used. In the analog embodiment the design of the Bessel filters is such that the filter group delay is the same in each of the N filters, so that the phase response is linear across the bandwidth of the filter. Additionally the summed filter response of the N filters produces a linear phase response over the entire bandwidth of the input ultrasound signal received from the transducer.

In the (preferred) case where a digital equalizer is incorporated into the signal pre-processing chain, equalized TGC is potentially utilized after the digitization stage 406. Furthermore, digital equalization can occur before or after virtually any of the steps illustratively depicted in FIG. 4 after digitization step 406, including: signal attenuation/amplification steps that are carried out on all signal components (e.g., currently used standard TGC stages that would correspond to the equalized TCG amplification step 410); signal log compression steps in the post-processing stages; signal accumulation/averaging (e.g., averaging step 408); digital amplification/scaling/bit shifting/barrel shifting, additional automatic or manual user controlled TGCs (e.g., digital TGC step 410); and beam formation (e.g., step focusing 412).

In various embodiments, a log compression operation is performed (e.g., analog compression before step 402, or digital compression just before step 414 or after step 414). Also, additional digital filtering and gain steps are performed, in various alternative embodiments, for example, just before/after focusing step 412.

In the case where equalized TGC is carried out after log compression, the TGC equalization operation can introduce non-linearities in the signal. The non-linearities can be emphasized or minimized, based upon the choice of coefficients assigned to individual ones of the set of amplifiers associated with corresponding ones of the equalizer bands. In an exemplary embodiment, the equalizer is applied prior to log compression or scan conversion steps. Scan conversion, where image data points are converted from polar to Cartesian coordinates (or other appropriate display layout position description), is generally performed on data generated from the preprocessed data stored during step 414.

The digital equalizer embodiment also uses N filters (corresponding to N frequency bands). Each of the N filters is, for example, an R tap and S bit depth IIR or FIR filter. Each filter utilizes the same filter design (i.e. least squares, equi-ripple, etc for FIR; and Chebyshev Type I, II, Butterworth, Bessel, etc. for IIR). For FIR filter embodiments, the phase response by definition is linear across the bandwidth of the filter (by definition of the FIR). For IIR filter embodiments, the filter design is setup so that the group delay is the same in each of the N filters. Additionally the summed filter response of the N filters produces a linear phase response over the entire bandwidth of the input ultrasound signal received from the transducer.

Figure 5:
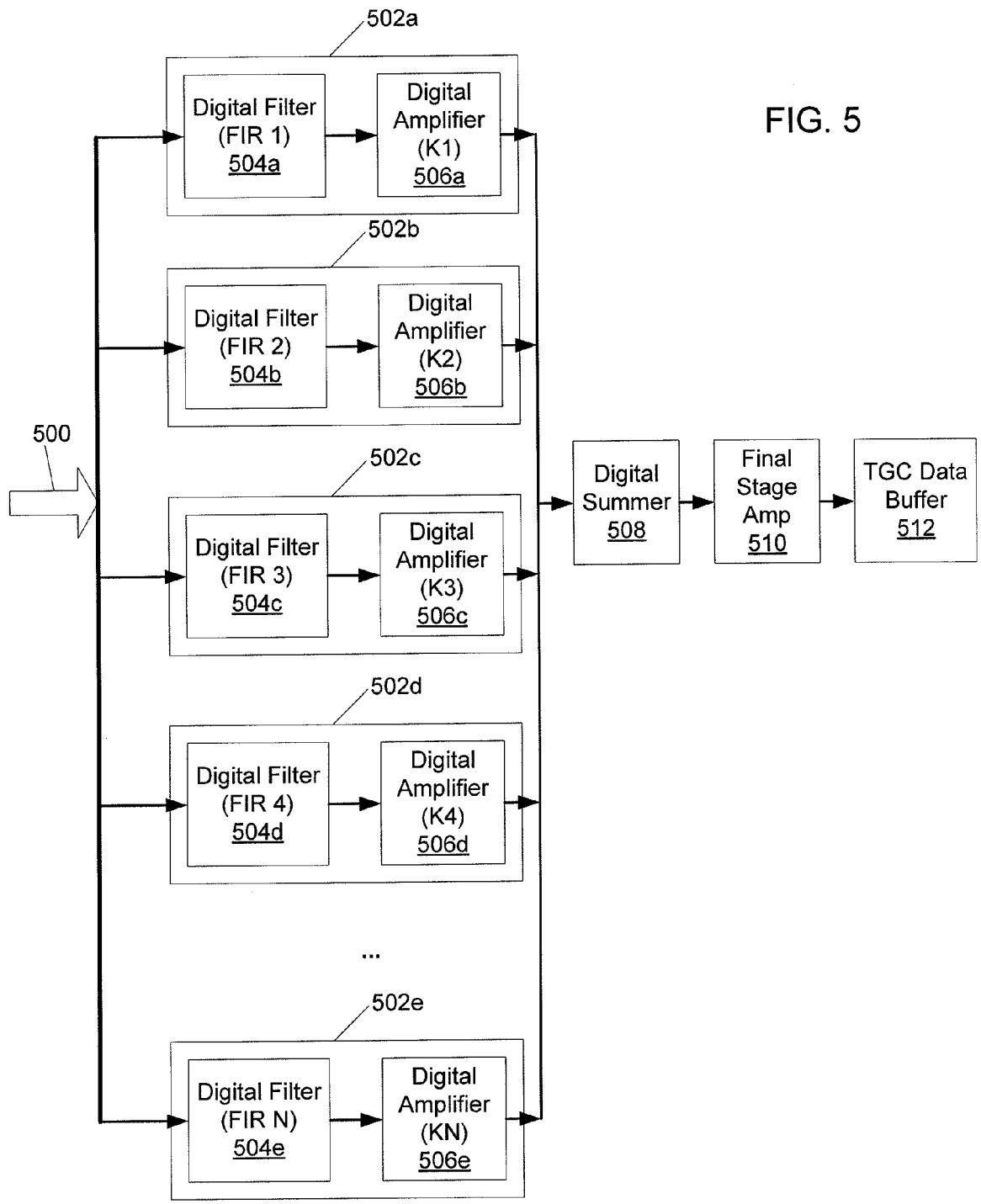
FIG. 5 is a schematic diagram of an exemplary digital ultrasound echo signal time-gain compensation and equalization sub-system.

Turning to FIG. 5 in an exemplary embodiment, the TGC equalizer stage comprises five equalizer bands (i.e., N equals "5"). Thus, a stream of 16-bit digitized data 500 is processed by each of five distinct equalizer components 502(a-e). Each of the five distinct equalizer components 502(a-e), includes a 15 tap, 16-bit depth "least squares" FIR filter 504(a-e) and an amplifier 506(a-e). It is noted that the choice of five bands for the equalizer components 502(a-e) is exemplary, and the number of bands "N" differs in alternative embodiments.

In an exemplary embodiment, the N (five) equalizer components 502(a-e) are each associated with a sub-band (e.g., an Octave) of the operating frequency bandwidth of the IVUS system. Examples of filter arrangements based on Octaves include the following:

1. For a 50% bandwidth, 80 MHz center frequency, the five FIR filters 504 would cover the following bands (in MHz): 62-63, 63.75-66.25, 67.5-72.5, 75-85, and 90-110 (pseudo Octave-based); and 2. For a 100% bandwidth, 80 MHz center frequency, the five FIR filters 504 would cover the following bands (in MHz): 61.25-63.75, 62.5-67.5, 65-75, 70-90, and 80-120. Furthermore, examples of filter arrangements with equal overlaps include the following:

1. For a 50% bandwidth, 80 MHz center harmonic frequency, the five FIR filters 504 would cover the following bands (in MHz): 59-69, 67-77, 75-85, 83-93, 91-101; and 2. For a 100% bandwidth, 80 MHz center harmonic frequency, the five FIR filters 504 would cover the following bands (in MHz): 39-57, 55-73, 71-89, 87-105, 103-121; and 3. For a 50% bandwidth, 40 MHz center frequency, the five FIR filters 504 would cover the following bands (in MHz): 29.5-34.5, 33.5-38.5, 37.5-42.5, 41.5-46.5, 45.5-50.5; and 4. For a 100% bandwidth, 40 MHz center frequency, the five FIR filters 504 would cover the following bands (in MHz): 19-29, 27-37, 35-45, 43-53, 51-61; and 5. For a 50% bandwidth, 20 MHz center frequency, the five FIR filters 504 would cover the following bands (in MHz): 14.5-17.5, 17-19.5, 19-21.5, 21-23.5, 23-25.5; and 6. For a 100% bandwidth, 20 MHz center frequency, the five FIR filters 504 would cover the following bands (in MHz): 9.5-14.5, 13.5-18.5, 17.5-22.5, 21.5-26.5, 25.5-30.5; and 7. For a 50% bandwidth, 10 MHz center frequency, the five FIR filters 504 would cover the following bands (in MHz): 4.5-7.5, 7-9.5, 9-11.5, 11-13.5, 13-15.5; and 8. For a 100% bandwidth, 10 MHz center frequency, the five FIR filters 504 would cover the following bands (in MHz): 7.5-12.5, 7.25-8.5, 8.25-9.5, 9.25-10.5, 10.25-11.5, 11.25-13.

In the exemplary embodiments, each of the FIR filters 504(a-e) is programmable in real time. Ideally (see, FIG. 6), the frequency responses of the filter bands are overlapping and have a fall-off that enables re-summing the amplified signals such that there are no gaps in the power frequency response of the summed equalized signal. Thus, if each amplifier had a unitary value (K=1), then the output would be the same as the input stream of digitized data 500. In any event, the filters 504(a-e) are designed to avoid gaps or peaks in the frequency response of the summed output of the filters 504(a-e). In the exemplary embodiment, phase response is linear (due to a constant group delay in each FIR filter). Furthermore, each of the FIR filters 504(a-e) uses the same number of taps.

The output data from the FIR filters 504(a-e), representing a particular frequency band, passes to a corresponding one of the amplifiers 506(a-e). Each of the amplifiers 506(a-e) is driven by a set of frequency range-dependent gain coefficients (K1-K5). In contrast to known TGC coefficients that compensate for time/range-dependent signal loss, the frequency range-dependent gain coefficients are designated to compensate for relative average attenuation that is experienced by IVUS echo signal in each of the N (e.g., five) frequency bands represented by the equalizer stages 502(a-e). In the exemplary embodiment, a string of time/range-dependent coefficients are specified for each one of the filter 504(a-e). However, in alternative embodiments, only a single value is specified for each of the N frequency range-dependent gain coefficients (K1-K5).

The output of the amplifiers 506(a-e) is re-combined by a summer 508. The summed signal has a corresponding brightness level which is potentially brighter/dimmer than the brightness level desired by a user. To facilitate adjusting the brightness of the resulting image, the summed digital signal values rendered by the summer 508 are thereafter passed to a final stage amplifier 510.

The final stage amplifier 510 carries out a user adjustable aspect of the TGC function. The amount of gain applied is adjustable for any particular range (i.e., distance from the ultrasound transducer element) to control the amount of dimming that occurs as echo data attenuates with distance from the transducer. A manual control is provided that enables a user to adjust the gain of the final stage amplifier 510 to align the brightness level of a displayed IVUS image with an average brightness level desired by the end-user.

The output of the final stage amplifier 510 is stored in a TGC equalizer output data buffer 512 (for further processing by the system to render IVUS images).

The above-described example is directed to a digital TGC equalizer arrangement that can be carried out in digital hardware, software, firmware, or any combination thereof. In an analog embodiment, the digital filters and amplifiers are replaced by known suitable analog circuit equivalents. It is noted that while digital filtering results in a linear phase response, analog filtering generally has a non-linear phase response characterized by roll-off outside a linear response range.

Figure 7:
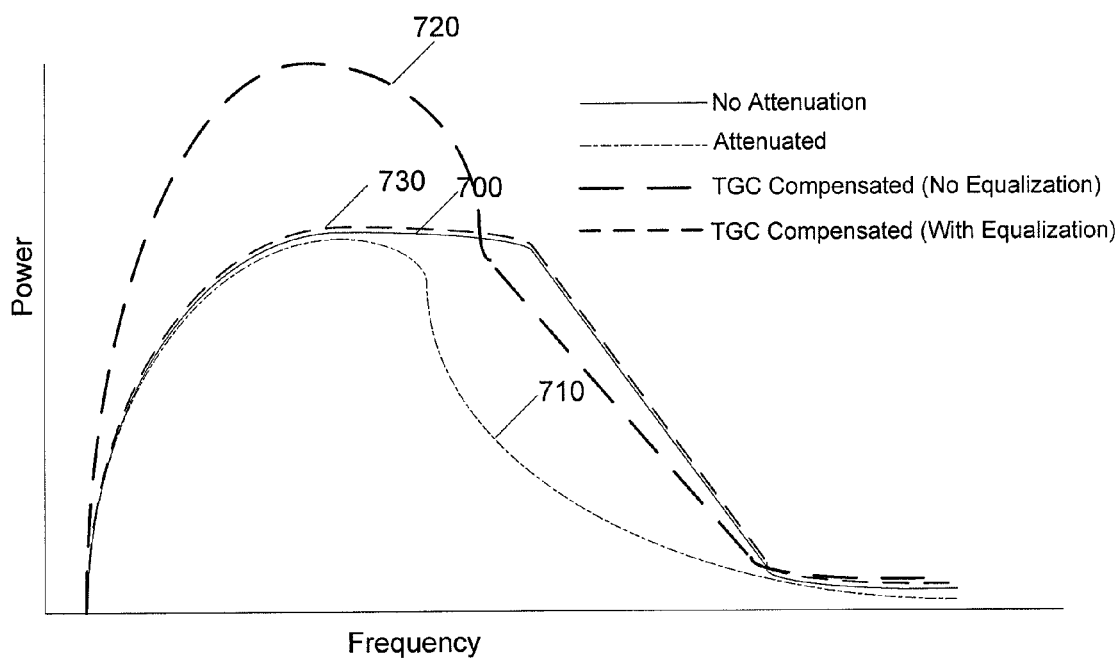
FIG. 7 illustratively depicts a set of frequency response curves for various signal types to illustrate the potential advantages of the sub-system depicted in FIG. 5.

Turning to FIG. 7, a diagram graphically depicts the effects of attenuation based on differential range (distance) based IVUS signal loss as a function of frequency. The disclosed TGC equalizer can be incorporated into a variety of ultrasound imaging applications including IVUS and external ultrasound operations. However, the equalizer is more applicable to ultrasound transducers that operate at a high center frequency and include a large bandwidth which leads to greater differences in loss as a function of frequency band (i.e., loss at the lowest frequency band versus loss at the highest frequency band). The TGC equalizer depicted, by way of example in FIG. 5, compensates for attenuation losses across frequency resulting from any of a variety of sources including, for example, backscatter and attenuation. The echo signal strength as a function of distance from the transducer is a function of both the attenuation (previous losses) and the backscatter strength of the scatters with regard to a particular frequency band. The TGC equalizer does not distinguish between the two sources when it performs its equalization operation on the received (digitized) ultrasound signal.

FIG. 7 provides an illustrative power spectrum for various types of compensation schemes (including none at all) at a particular distance (or "time" in the context of time gain compensation) from the transducers. Solid line 700 corresponds to an exemplary power spectrum for an ultrasound signal over a frequency range with no attenuation. Dashed line 710 represents an uncompensated attenuated signal. In particular, line 710 shows the signal drop-off at higher frequencies due to attenuation of the signal. Dashed line 720 represents the effect on the attenuated signal when a single amplifier-based TGC system, and dashed line 730 represents the effect on an attenuated signal when a TGC equalizer approach is employed that is potentially carried out using a TGC equalizer of the type depicted in FIG. 5. The frequency band-specific attenuation compensation processing stage for an ultrasound processing system described herein thus enables compensation for high frequency signal loss without overcompensating/saturating lower frequency band ultrasound echo signal components.

In an exemplary embodiment, the basic compensation coefficient at each frequency band is $r=\alpha$ where $\alpha$ is the attenuation coefficient measured in dB/cm MHz$^2$. The signal loss is characterized by $S_\alpha$=Signal Loss (x)=S exp (−α×f) where S is the original unattenuated signal and x is the depth or time-based location of the signal amplitude since the signal is a function of time/depth in Ultrasound). The compensation is characterized by $K_f(x)$=exp (r×f), which when applied to the attenuated signal would remove the attenuation term exp (−α×f) leaving S. Therefore, compensation can be performed as long as the signal is neither attenuated below the noise floor nor saturated.

Attenuation in some cases may not be well characterized with a single coefficient α. Or alternatively the compensation term may not be characterized by exp (−α×f) but may be of the form exp (−α×f$^n$) where n>=1. Either case is managed by the approach presented herein. But for simplicity we shall use the form exp (−α×f$^n$).

In the exemplary embodiment, each of the N frequency bands (bins) has a different attenuation characteristic. Therefore, a separate compensation coefficient generator is defined for each frequency band/bin. The designated compensation for each band/bin is defined, for example, as: (1) a maximum, (2) an average, (3) a median or (4) a minimum. Other approaches are also possible, such as a Gaussian weighted average, or Poisson weighted average. However, in each instance an attenuation coefficient α or attenuation value in each frequency band/bin is defined. Thus the compensation for any frequency band/bin is characterized as:

$K_{fN}(x)$=exp (r×f$_N^n$) where N is the frequency bin number, and n is the order of the frequency needed to define the relationship between the compensation coefficient r and the frequency f.

Furthermore the compensation can, alternatively, be defined according to range in a discrete manner if desired, for a digital embodiment, so that for a signal S(s) the following compensation value is defined:

$K_{fN}(s)$=exp (r s f$_N^n$) where N is the frequency bin number, and n is the order of the frequency needed to define the relationship between the compensation coefficient r and the frequency f.

Note that K is range (distance) and frequency band/bin dependent.

Figure 8:
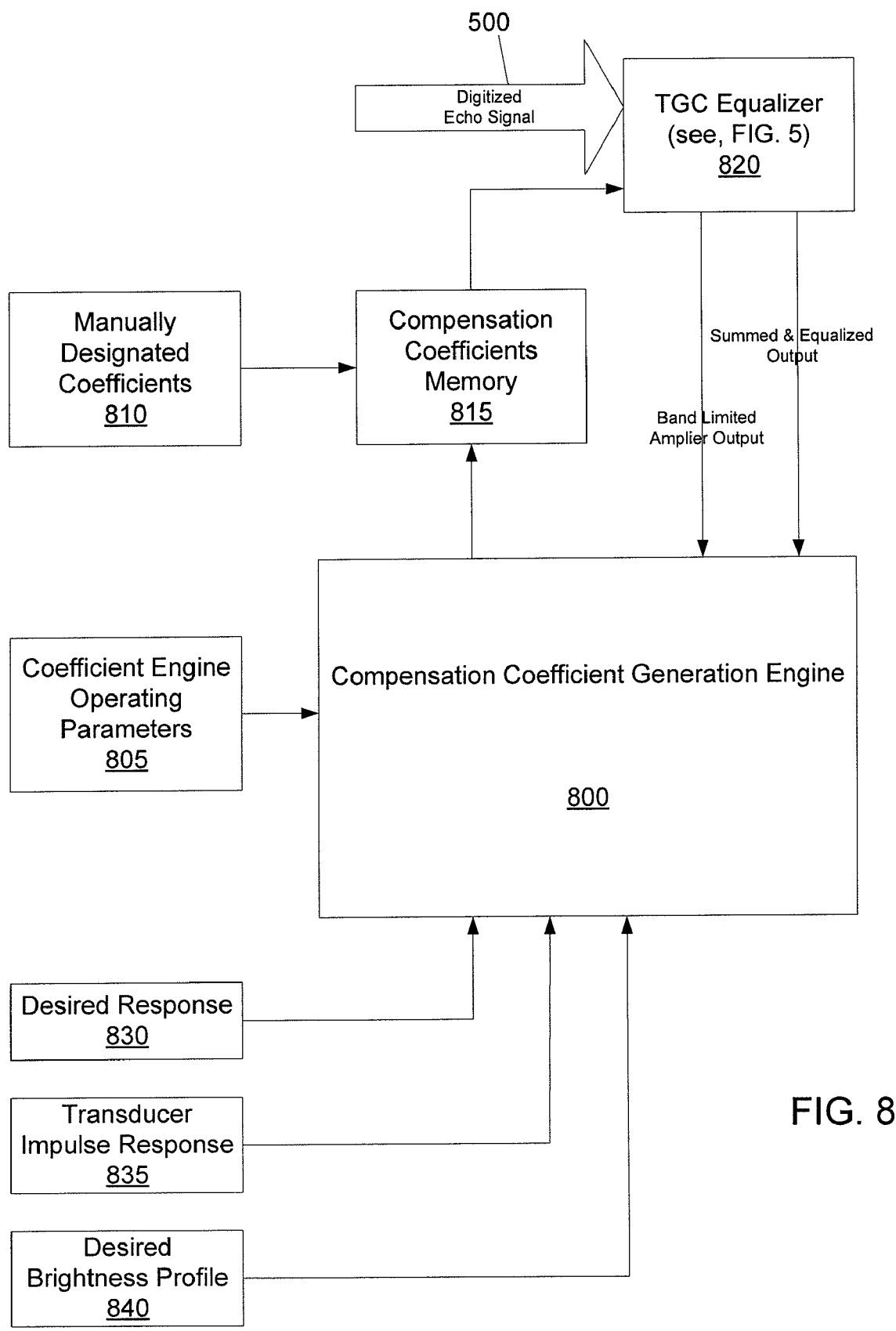
FIG. 8 is a schematic diagram of an exemplary digital ultrasound echo signal time-gain compensation and equalization sub-system including an automatic coefficient generation engine that, through iterative tuning, generates a set of compensation components based on a target frequency response spectrum.

Having described the principals behind TGC equalizer operation, attention is directed to FIG. 8 that depicts computational components of an exemplary ultrasound echo signal pre-processing system including a TGC equalizer 820 and a coefficient generation engine 800 that supplies the amplifier coefficients applied by the N (e.g., five) amplifiers within the TGC equalizer 820. The coefficient generation engine 800 is carried out, in various embodiments, in the form of software, but can also be carried out using hardware, firmware or any combination thereof. Furthermore, the frequency band-specific amplifier coefficients provided to the TGC equalizer 820 are generated from information provided by one or more offline (e.g., manual) and online (e.g., coefficient generation engine 800) sources.

The exemplary TGC equalizer sub-system illustratively depicted in FIG. 8 relies upon compensation coefficients that drive a set of N band-specific amplifiers within the TGC equalizer 820. The values of the compensation components are derived from a variety of information sources including both configurable parameters and current compensated ultrasound echo signal output.

A set of operating parameters 805 are designated by users during offline configuration of the coefficient generation engine 800. A scan line range indicates the general distance from the transducer elements from which data is acquired. The scan line range is specified in any of a number of ways including, for example, a number of samples in each scan line. The number of samples, taken at a regular interval (e.g., every microsecond), indirectly specify the distance covered by a sequence of digitized signal samples (taking into consideration the general speed of sound passing through the tissue). A user can also specify windows (sub-ranges) within the scan line range for which a different set of configuration parameters (and possibly compensation coefficients) are potentially specified. In the illustrative example, the full scan line range is divided into a set of sub-ranges by designating (1) a window range, (2) a window overlap, and (3) averaging/smoothing function. The window overlap facilitates averaging coefficients at transition points between windows, thus avoiding discontinuities at window transition points. In exemplary embodiments, during setup/configuration of the IVUS imaging system, a user specifies an averaging function that is applied to smooth transitions between windows.

Other ones of the operating parameters 805 relate to the extent to which a set of compensation coefficients will apply to a single scan line or a set of scan lines within a frame of ultrasound image data. In the illustrative example, a user specifies a Number of Scan Lines in a Subset of the scan lines that make up an entire frame of scan lines. The number of scan lines in a full frame is specified by a Number of Scan Line in Frame parameter. An Engine Update Rate parameter specifies how often the coefficient generation engine 800 updates the compensation coefficient memory 815 with a re-calculated set of values (after an initial start-up procedure is performed in accordance with the steps summarized in FIG. 9 described herein below).

The act of manually designating coefficients is represented, in FIG. 8, by manually designated coefficients 810. In an exemplary embodiment, the manually designated coefficients 810 are initially generated from manual analysis of echo signal frequency response. The manually designated coefficients 810 are stored in a compensation coefficients memory 815 during initialization. The coefficients in memory 815 drive gain level for designated/corresponding ones of the frequency band-specific amplifiers of a TGC equalizer 820. The manually designated equalizer amplifier coefficients 810 will not, alone, enable the TGC equalizer 820 to restore the original signal. Non-ideal restoration of signal response via the manual coefficients 810 can potentially include one or more of: signal saturation, attenuation of high frequency components of the echo signal below a noise floor, and/or a complex attenuation path.

For the purpose of selecting manual coefficients 810, the set of compensation coefficients is referred to as the compensation profile, which corrects for the attenuation effect presented by the complex attenuation path of the tissue. The complex attenuation path within this description is referred to as the "attenuation profile."

In further explanation of the above, during acquisition of IVUS echo signal data sets for purposes of IVUS imaging, the location of the transducer changes position relative to the vasculature, and in addition there is cardiac rhythm causing changes to, for example, vessel walls. Under these circumstances the transmit/receive path of the ultrasound changes over the course of data acquisition. The path changes results in changes in localized attenuations over the path of ultrasound excitation signals and their corresponding echoes, since the tissues passed through on the path will have changed. The cumulative effect of localized attenuation changes affects the ultrasound signals. The term "complex attenuation path" is intended to refer to the passage of the ultrasound through a multitude of tissues within its transmit/receive path, and wherein each tissue has a different attenuation characteristic. The complex attenuation path can be thought of as a multitude (sequence) of attenuation coefficients. In a simple model of one or two tissues, the attenuation coefficient that describes the path can be a weighted sum of the attenuation coefficients of the two tissues (weighting based on the range that each tissue comprised in the attenuation path). In a complex model of a multitude of discrete tissues, the weighted sums are much more complicated. For example, each tissue type may not have a same attenuation profile—attenuation coefficients follow a $f^n$ profile, where for each tissue type n could be 1, 2 or higher order.

In an exemplary embodiment, the potentially complicated attenuation profile is simplified by modeling it as an aggregate attenuation coefficient at each frequency band, as the complex attenuation profile can be determined, for example, by finding a total aggregate attenuation profile that is valid across an entire path of the ultrasound signal (which will look like some curve over frequency). Any curve can be modeled using curve fitting techniques as a polynomial fit. For 5 frequency bins there are 5 polynomial coefficients which happen to be the 5 attenuation coefficients for each frequency. The profile, in an exemplary embodiment, specifies a separate curve for each range in a scan line—resulting in, for example, 5 attenuation coefficients for each frequency and range bin. The attenuation coefficients are referred to herein as the attenuation profile. Similarly, the set of compensation coefficient values for each frequency and range bin that compensates for the attenuation profile is referred to as a compensation profile.

Compensation coefficients are relatively easily rendered that avoid signal saturation and a noise signal floor. It is desirable to ensure the entire signal across the region of interest is above the noise floor and below saturation. This may be achieved through proper adjustment of input power and amplification of the received echo signal prior to the TGC equalizer 820. Also, during designation of the manual coefficients 810, the attenuation profile is characterized by a model, is reasonably continuous and does not change substantially from scan line to scan line. Under these circumstances, the compensation profile is determined with a reasonable degree of accuracy. In the case of IVUS imaging systems, an attenuation profile is chosen from a simple model for the vessel. For instance it is expected the attenuation path for the ultrasound signal is blood-plaque-arterial wall. However, this model is overly simplistic. The size of the blood region, plaque region, and arterial wall region dictates the attenuation profile as much as the actual attenuation coefficients for each region. Therefore statistical analysis is also performed to render the manual coefficients 810.

Statistical analysis is performed, for example, by isonifying several blood vessels to observe their attenuation profiles on a scan-line by scan-line basis. A statistical average of the observed attenuation profiles is thereafter used to establish an expected attenuation profile and a corresponding compensation profile comprising a set of compensation coefficients. A variety of statistical methods can be used to establish these profiles.

The attenuation profile also differs in accordance with a choice of: (1) transducer aperture, (2) beam profile and (3) insonification frequency, so that a different set of coefficients are generated for at least each transducer type, if not for each transducer assembly. This is also true for the imaging system, since an imaging system in ultrasound is setup/matched/tuned/optimized for a given transducer or transducer family.

The ultrasound echo signal pre-processing system depicted in FIG. 8 supports other manual input that affect the specification of compensation coefficients by the coefficient generation engine 800. For example, end-users can manually specify a desired compensated response curve 830 such as a high pass or low pass configuration. The coefficient generation engine 800 uses the information to modify coefficient values in the compensation coefficients memory 815. The compensation coefficients stored in the coefficients memory 815 are, for example, implemented as amplification values in the TGC equalizer 820. However, the coefficients can be incorporated into the filter design coefficients of the TGC equalizer 820 in the case of a digital embodiment of the equalizer 820. The coefficients in the manual case are a single set of coefficients valid for every scan line. The single set of coefficients is determined through statistical analysis of several phantoms and vessels. However, one cannot predict in on-line imaging how one scan line varies with the next, so the coefficients generated are applied on each scan line in the same manner. However, through on-line automated processing, one could potentially (limited only be processing time) generate a separate set of coefficients for each scan line separately, or for a sub-set of scan lines or for a full frame of scan lines.

Figure 9:
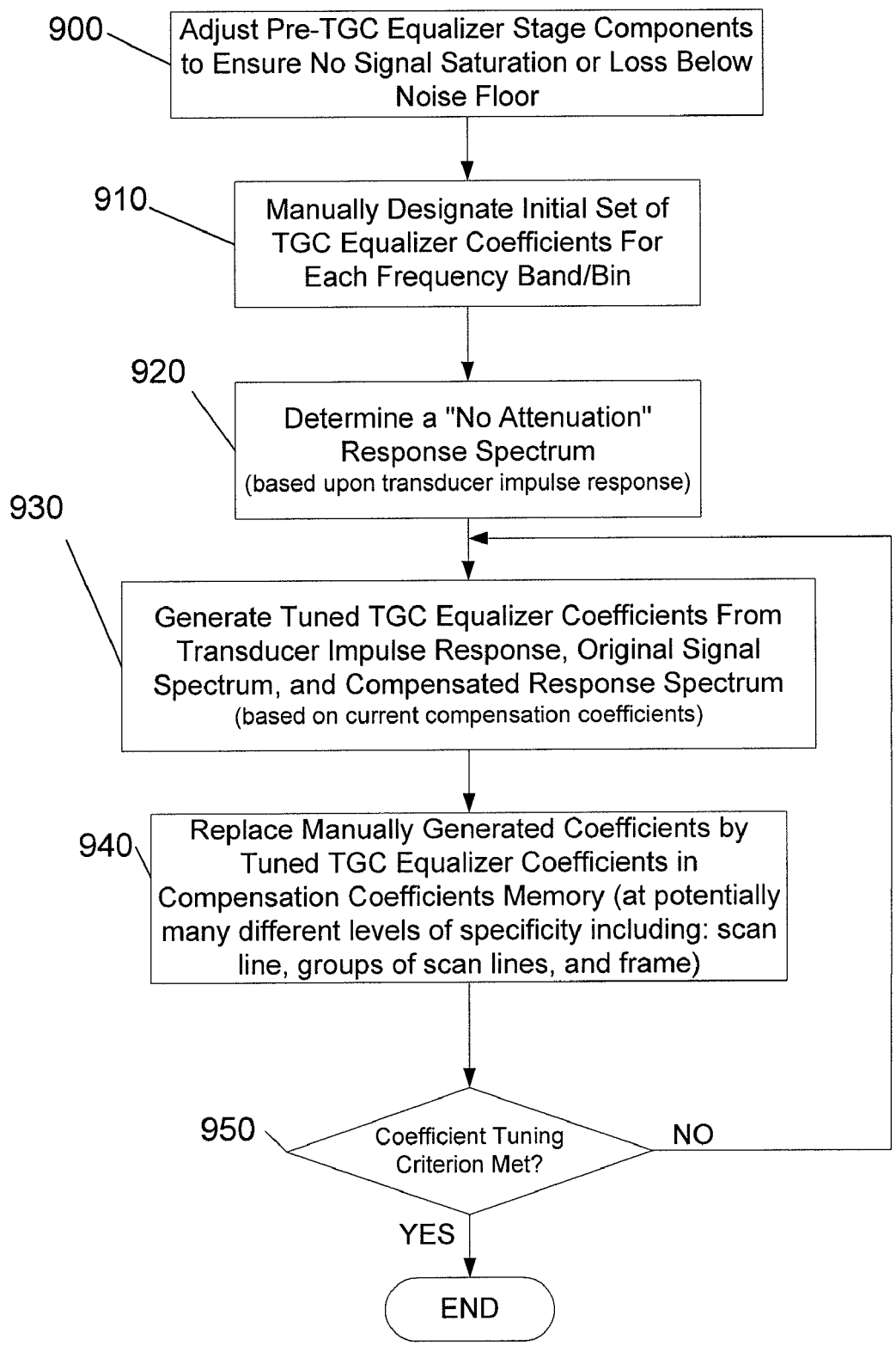
FIG. 9 is a flowchart summarizing an exemplary set of steps for the operation of an ultrasound echo signal time-gain compensation and equalization sub-system depicted in FIG. 8.

The illustrative system supports automatic generation from a variety of information sources. An exemplary automatic coefficient generation scheme is explained herein below with continued reference to FIGS. 8 and 9. FIG. 8 is a schematic drawing showing (hardware/software/firmware) computational components and data sources. FIG. 9 summarizes a set of steps for operating the TGC equalizer sub-components of an ultrasound imaging system.

With regard to the automatic generation of the TGC equalizer 820's amplification coefficients (K1, K2, . . . , Kn), the received signal is assumed to be neither saturated nor below a noise floor. If the signal is saturated or below the noise floor, then the compensation profile may not be optimal. Therefore, in an illustrative embodiment, the pre-processing stages are adjusted (e.g., input power, amplification of the signal prior to the TGC equalizer 820) during step 900 to ensure the entire signal across the region of interest is above the noise floor and below saturation.

A prerequisite of automatic generation of TGC equalizer coefficients (in real-time), is a rough estimate of an attenuation profile for a given situation. Furthermore, a rough estimate is made separately for each frequency band/bin represented in the TGC equalizer 820. In an exemplary embodiment, during step 910 an initial set of rough estimate coefficients for the TGC equalizer 800 is empirically determined and provided in the form of manually designated coefficients 810 stored in the compensation coefficients memory 815—a form of "start-up" mode of operation for the TGC equalizer 820. The initial set of coefficients is, for example, based on gathered statistical (e.g., averaged) data, and is used in the aforementioned "start-up" mode to seed the automatic generation of coefficients by the coefficient generation engine 800.

If compensation is perfect, then applying the coefficients of the compensation profile by the TGC equalizer 820 fully corrects a previously observed attenuation profile. Therefore, if compensation is perfect, then for a point scatterer or homogeneous scatterer medium the response spectrum of the output from the TGC equalizer is similar to a transducer impulse response of the point scatterer or homogenous scatterer medium.

Thus, in an exemplary embodiment, at step 920 the response spectrum in the case of no signal attenuation is determined. An initial response spectrum estimate is made based on measurement of the transducer impulse response of a point scatterer or a homogeneous scatterer medium (transducer impulse response 835) that is thereafter provided to the coefficient generation engine 800.

In an exemplary embodiment, during step 930 the coefficient generation engine 800 generates a set of tuned coefficients for storage in the compensation coefficients memory 815 by comparing the transducer impulse response 835 to (1) an original spectrum of the echo signal (in a first occurrence of step 930), and (2) the compensated response spectrum of the signal (in subsequent iterations of step 930) using the currently designated compensation coefficients in memory 815. In an exemplary embodiment, the compensated response spectrum is generated from the individual band-specific amplifier outputs. However, in an alternative embodiment, the compensated response spectrum is generated from the output (labeled "KS Output" in FIG. 8) of the final stage amplifier 510. Furthermore, in illustrative embodiments, the comparison during step 930 is driven by the desired response 830 and desired brightness profile 840.

In the first iteration of step 930, the compensated response spectrum is generated from the set of manually designated coefficients 810 initially stored in memory 815. In subsequent iterations of step 930, the coefficients in memory 815 correspond to values generated automatically by the coefficient generation engine 800. In an exemplary embodiment, during step 930, at each frequency bin the transducer impulse response and the original spectrum are used to generate a delta in signal level at each frequency bin. The delta is used to calculate a gain value (compensation coefficient) applied at the particular frequency bin. Then after the first iteration of step 930, the compensated spectrum is compared to the impulse response, and new deltas are generated which are added/subtracted from the original delta. Rate of change limits are potentially applied (e.g., update period and differences between previous/new compensation coefficients).

During step 940, the tuned coefficients replace the coefficients in the compensation coefficients memory 815 for each frequency band/bin of the initial compensation profile provided by the manually designated coefficients 810. In accordance with various exemplary embodiments, the compensation coefficients automatically generated by the coefficient generation engine 800 (and stored in the coefficient memory 815) are, for example, generated individually for each scan line, over a small subset of scan lines or over all scan lines present in a frame. When using multiple scan lines, various statistical models are potentially used, such as Poisson or Gaussian weighting, spectral weighting, median, mean, etc. to establish the compensation coefficients stored in the memory 815.

Furthermore, in an exemplary embodiment, weighting coefficients limit the amount of change to the compensation coefficients during each iteration of steps 930/940 to ensure eventual convergence to a desired set of compensation coefficients (i.e., maintain system stability).

In an exemplary embodiment, at step 950, if the difference between the original signal spectrum and the compensated response spectrum are not within a specified threshold, then control returns to step 930 wherein a new comparison is run based on the new compensated response spectrum arising from the previously stored compensation coefficients (during step 940 for a previous iteration). Thus, the compensation coefficients from memory 815 are updated during step 940 and re-applied (if necessary) to the TGC equalizer 820 to render new spectral response data for further analysis during a next iteration of step 930. If, at step 950, the difference between the impulse (desired) response and the actual (compensated) response is less than a value specified by a tuning criterion, then control passes to the End—i.e., the coefficients are sufficiently tuned for live operation on actual ultrasound (e.g., IVUS) echo signal data. By way of example, a "tuned" status is reached when the differences between compared responses at each frequency bin are less than 1 dB.

Having described an exemplary initial start-up and tuning method for generating a useful set of compensation coefficients for the TGC equalizer, it is noted that since the coefficients are permitted to vary not only with frequency bin but also with range, the comparison can be made not only on the overall range but also on multiple overlapping range windows, such that each range window has its own transducer impulse response and initial manually designated compensation coefficients derived from initial statistical data obtained from empirical testing at particular ranges. The combined result of the analysis using the overall range and overlapping range windows can be used to establish the changes to the weighting coefficients desired.

The illustrative embodiment depicted in FIG. 8 supports user designated spectral response shapes 830. Such shapes, for example, emphasize particular frequency ranges within the overall frequency band of the transducer frequency response (e.g., a high or low pass configuration). Instead of the transducer impulse response, the coefficient generation engine 800 uses the user-designated response spectrum shape to drive coefficient generation during step 930.

The illustrative embodiment depicted in FIG. 8 supports user designation of desired average brightness or brightness profile over range (e.g., dimming with increased range) information 840. The coefficient generation engine 800 applies the provided brightness over range information 840 when calculating the compensation coefficients, stored in memory 815, by performing spectral and histogram analysis across the supported range (time) of the TGC equalizer 820's processing of received ultrasound echo signal information.

Adjustments to the compensation coefficients 815, by way of example, are applied in real-time on the data sets. In both the analog and digital embodiments there will be a time delay between calculation of the coefficients and the actual application of the coefficients, since at least one frame of data is needed to necessitate the calculation. Typically the calculation engine would be performed as a digital embodiment, whereas the image equalizer itself could be a digital or analog embodiment.

Saturation is generally not desired, and the compensation coefficients stored in memory 815 can be setup so that saturation is avoided, by imposing conditionals that limit the gain of any of the amplifiers. The limits are, for example, applied via the update weighting coefficients (in the case of the automatic selection of coefficients method) that limit the magnitude of change for the coefficients during any particular iteration of steps 930 and 940. The final amplification may or may not require saturation limiting, since the end-user in some circumstances may desire a certain amount of saturation. In manual selection of coefficients it is not possible to compensate for saturation since the coefficient generation engine 800 that makes such determinations does not participate in the amplifier coefficient generation process.

Upon completion of the tuning/training procedure summarized in FIG. 9, the TGC equalizer depicted, by way of example, in FIG. 5 operates upon received digitized ultrasound echo signal data to render TGC equalized output for further processing to render an ultrasound image.

Systems and their associated components and/or methods have been described herein above with reference to exemplary embodiments of the invention including their structures and techniques. It is noted that the present invention is implemented in computer hardware, firmware, and software in the form of computer-readable media including computer-executable instructions for carrying out the described functionality/methodology. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A method for providing an equalized ultrasound echo signal for rendering intravascular images comprising:
   inserting at least a portion of a catheter into a vascular structure;
   activating a transducer portion of the catheter, said activating of the transducer portion resulting in transmission of an ultrasound signal transmitted toward vascular tissue;
   acquiring an ultrasound echo signal corresponding to reflections by backscatterers of the ultrasound signal transmitted toward vascular tissue;
   filtering and amplifying the ultrasound echo signal to remove frequency components that constitute noise;
   performing a first time-gain compensation on the ultrasound echo signal to accommodate for a drop off in the ultrasound echo signal as a function of distance; and
   performing a second time-gain compensation on the ultrasound echo signal according to sub-bands within a frequency response spectrum of the ultrasound echo signal, the second time-gain compensation comprising:
      separating, using an odd-numbered set of band-pass filters, the ultrasound echo signal into a set of frequency band-specific signal components, wherein frequency bands of adjacent band-pass filters partially overlap and wherein the middle band-pass filter of the odd-numbered set of band-pass filters covers a center frequency of the transducer portion of the catheter,
      applying frequency band-specific amplifier gains to the set of frequency band-specific signal components to create a set of gain compensated frequency band-specific components, and
      combining the set of gain compensated frequency band-specific components to create an equalized ultrasound echo signal.

2. The method of claim 1 further comprising the step of generating a stream of digitized echo signal samples from the ultrasound echo signal prior to the compensating step, and wherein the band-pass filters perform digital filtering on the stream of digitized echo signal samples.

3. The method of claim 1 wherein the applying step is carried out according to gain values specified by compensation coefficients stored in a compensation coefficients memory, and wherein the compensation coefficients are specified according to time range on a scan line.

4. The method of claim 3 further comprising manually specifying the compensation coefficients stored in the compensation coefficients memory.

5. The method of claim 3 further comprising automatically specifying the compensation coefficients stored in the compensation coefficients memory based upon the set of gain compensated frequency band-specific components and a specified desired frequency response curve.

6. The method of claim 5 wherein the automatically specifying step is performed in accordance with a brightness profile specified according to time range.

7. The method of claim 3 wherein the compensation coefficients are stored separately in the compensation coefficients memory for each one of a set of scan lines on an image frame.

8. The method of claim 1 further comprising applying, by a final stage amplifier, a final time-gain compensation on the equalized ultrasound echo signal.

9. The method of claim 1, wherein a sampling period for generating individual digital data points from the ultrasound echo signal corresponding to a scan line of backscattered ultrasound data is in a range of 2.5 to 10 nanoseconds.

10. The method of claim 1, wherein a sampling period for generating individual digital data points from the ultrasound echo signal corresponding to a scan line of backscattered ultrasound data is in a range of 5 to 20 nanoseconds.

11. The method of claim 1, wherein a sampling period for generating individual digital data points from the ultrasound echo signal corresponding to a scan line of backscattered ultrasound data is in a range of 1.25 to 5 nanoseconds.

12. The method of claim 1, wherein a sampling period for generating individual digital data points from the ultrasound echo signal corresponding to a scan line of backscattered ultrasound data is in a range of 0.68 to 2.5 nanoseconds.

13. An ultrasound system for rendering intravascular images comprising:
   an ultrasound catheter for insertion into a vascular structure comprising a distally mounted ultrasound transducer probe; and
   an intravascular ultrasound console including:
      an ultrasound catheter interface for signaling the ultrasound transducer probe to transmit an ultrasound signal transmitted toward vascular tissue and thereafter acquire an ultrasound echo signal corresponding to reflections by backscatterers of the ultrasound signal transmitted toward vascular tissue,
      a first ultrasound echo time-gain compensation component configured to adjust the ultrasound echo signal to accommodate for a drop off in the ultrasound echo signal as a function of distance, and
      a second ultrasound echo signal time-gain compensation component configured to adjust the ultrasound echo signal according to sub-bands within a frequency response spectrum of the ultrasound echo signal, the second time-gain compensation component comprising:
  a set of band-pass filters for separating the ultrasound echo signal into a set of frequency band-specific signal components,
  a set of frequency band-specific amplifiers for applying frequency band-specific amplifier gains to the set of frequency band-specific signal components to create a set of gain compensated frequency band-specific components, and
  a signal summer for combining the set of gain compensated frequency band-specific components to create an equalized ultrasound echo signal.

14. The ultrasound system of claim 13 further comprising an analog-to-digital converter (ADC) for generating a stream of digitized echo signal samples from the ultrasound echo signal, the ADC being positioned in an ultrasound signal processing chain prior to the second ultrasound echo signal time-gain compensation component, and wherein the band-pass filters perform digital filtering on the stream of digitized echo signal samples.

15. The ultrasound system of claim 13 further comprising a compensation coefficients memory for storing compensation coefficients specified according to time range on a scan line, wherein the compensation coefficients specify gain for individual ones of the frequency band-specific signal components.

16. The ultrasound system of claim 15 further comprising a user input interface facilitating manually specifying the compensation coefficients stored in the compensation coefficients memory.

17. The ultrasound system of claim 15 further comprising a coefficient generation engine for automatically specifying the compensation coefficients stored in the compensation coefficients memory based upon the set of gain compensated frequency band-specific components and a specified desired frequency response curve.

18. The ultrasound system of claim 17 wherein the coefficient generation engine computes the compensation coefficients in accordance with a brightness profile specified according to time range.

19. The ultrasound system of claim 15 wherein the compensation coefficients memory is configured to specify a distinct set of compensation coefficients for each of a set of scan lines on an image frame.

20. The ultrasound system of claim 13 further comprising a final stage amplifier stage for applying a final time-gain compensation on the equalized ultrasound echo signal.

21. The ultrasound system of claim 13, wherein the sampling period for generating individual digital data points from the ultrasound echo signal corresponding to a scan line of backscattered ultrasound data is in a range of 0.68 to 20 nanoseconds.

22. The ultrasound system of claim 13, wherein the ultrasound transducer probe has an 80 MHz center frequency and wherein the set of band-pass filters consist of five FIR filters, and wherein the five FIR filters cover the frequency bands of 59-69, 67-77, 75-85, 83-93, 91-101 MHz.

23. The ultrasound system of claim 13, wherein the ultrasound transducer probe has an 80 MHz center frequency and wherein the set of band-pass filters consist of five FIR filters, and wherein the five FIR filters cover the frequency bands of 39-57, 55-73, 71-89, 87-105, 103-121 MHz.

24. The ultrasound system of claim 13, wherein the ultrasound transducer probe has an 40 MHz center frequency and wherein the set of band-pass filters consist of five FIR filters, and wherein the five FIR filters cover the frequency bands of 29.5-34.5, 33.5-38.5, 37.5-42.5, 41.5-46.5, 45.5-50.5 MHz.

25. The ultrasound system of claim 13, wherein the ultrasound transducer probe has an 40 MHz center frequency and wherein the set of band-pass filters consist of five FIR filters, and wherein the five FIR filters cover the frequency bands of 19-29, 27-37, 35-45, 43-53, 51-61 MHz.

26. The ultrasound system of claim 13, wherein the ultrasound transducer probe has an 20 MHz center frequency and wherein the set of band-pass filters consist of five FIR filters, and wherein the five FIR filters cover the frequency bands of 14.5-17.5, 17-19.5, 19-21.5, 21-23.5, 23-25.5 MHz.

27. The ultrasound system of claim 13, wherein the ultrasound transducer probe has an 20 MHz center frequency and wherein the set of band-pass filters consist of five FIR filters, and wherein the five FIR filters cover the frequency bands of 9.5-14.5, 13.5-18.5, 17.5-22.5, 21.5-26.5, 25; 5-30.5 MHz.

28. The ultrasound system of claim 13, wherein the ultrasound transducer probe has an 10 MHz center frequency and wherein the set of band-pass filters consist of five FIR filters, and wherein the five FIR filters cover the frequency bands of 4.5-7.5, 7-9.5, 9-11.5, 11-13.5, 13-15.5 MHz.

29. The ultrasound system of claim 13, wherein the ultrasound transducer probe has an 10 MHz center frequency and wherein the set of band-pass filters consist of five FIR filters, and wherein the five FIR filters cover the frequency bands of 7.5-12.5, 7.25-8.5, 8.25-9.5, 9.25-10.5, 10.25-11.5, 11.25-13 MHz.

30. The ultrasound system of claim 13, wherein the intravascular ultrasound console further includes a tissue characterization component configured to identify a tissue type based on the equalized ultrasound echo signal.

31. The ultrasound system of claim 13, wherein the set of band-pass filters comprises an odd number of filters.

32. The ultrasound system of claim 31, wherein the middle band-pass filter of the odd-numbered set of band-pass filters covers a center frequency of the ultrasound transducer probe.

33. The ultrasound system of claim 13, wherein frequency bands of adjacent band-pass filters of the set of band-pass filters partially overlap.

* * * * *